United States Patent [19]

Törngren

[11] Patent Number: 5,493,119
[45] Date of Patent: Feb. 20, 1996

[54] SMOKE AND VAPOR DETECTOR FOR MICROWAVE OVEN

[75] Inventor: Per Ake B. Törngren, Linköping, Sweden

[73] Assignee: Whirlpool Europe B.V., Veldhoven, Netherlands

[21] Appl. No.: 352,285

[22] Filed: Dec. 8, 1994

Related U.S. Application Data

[63] Continuation of Ser. No. 53,055, Apr. 26, 1993, abandoned.

[30] Foreign Application Priority Data

Apr. 27, 1992 [SE] Sweden ................................ 920/314

[51] Int. Cl.⁶ ...................................................... H05B 6/68
[52] U.S. Cl. ............................................ 250/343; 219/707
[58] Field of Search .................................. 219/702, 704, 219/705, 707, 711, 757; 250/345, 343

[56] References Cited

U.S. PATENT DOCUMENTS 4,383,158  5/1983  Niwa ........................ 219/707
4,496,817  1/1985  Smith ....................... 219/10.55 M

FOREIGN PATENT DOCUMENTS

| 0450499 | 9/1990 | European Pat. Off. . | |
| 0394009 | 10/1990 | European Pat. Off. . | |
| 459846 | 12/1991 | European Pat. Off. | 250/343 |
| 3730579 | 3/1989 | Germany . | |
| 1-262441 | 10/1989 | Japan | 250/343 |
| 0015007 | 2/1980 | United Kingdom . | |
| 2123548 | 2/1984 | United Kingdom . | |
| 2109925 | 6/1993 | United Kingdom . | |

Primary Examiner—Constantine Hannaher
Attorney, Agent, or Firm—Robert O. Rice

[57] ABSTRACT

A smoke and vapour detector for microwave ovens comprises a light transmitter (12) and two light receivers (13, 14) arranged in a housing (11) through which air from the microwave chamber flows during a heating procedure. One receiver (13) is designed to receive direct light from the transmitter (12), and the other receiver (14) is designed to receive indirect or scattered light from the interior of the housing (11). The signals from the receivers are differentiated and subtracted from one another in order to generate a difference signal indicating the presence of smoke or water vapour in the chamber air.

5 Claims, 1 Drawing Sheet

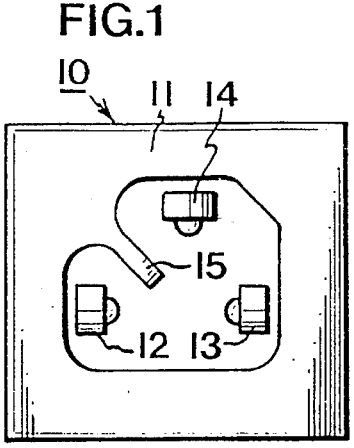
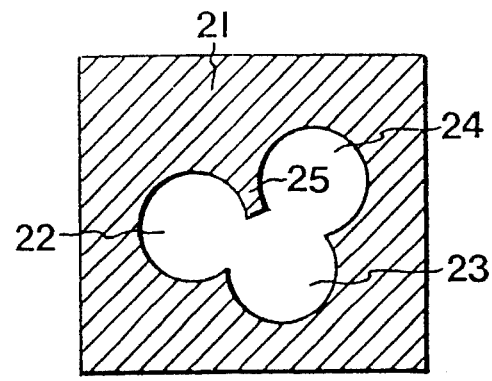
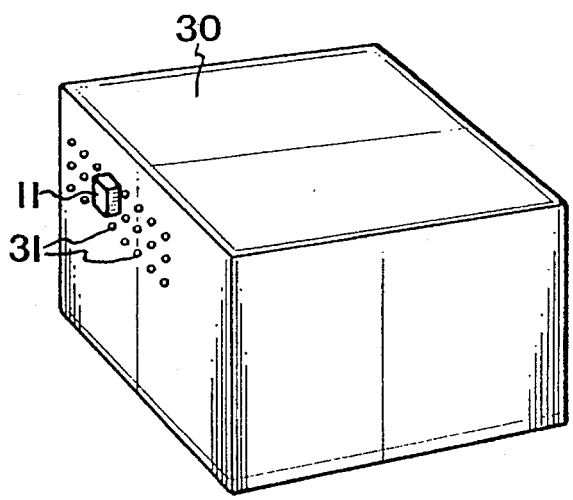
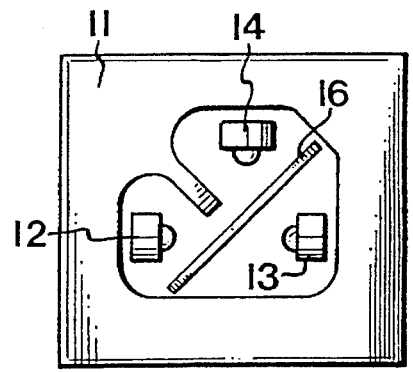
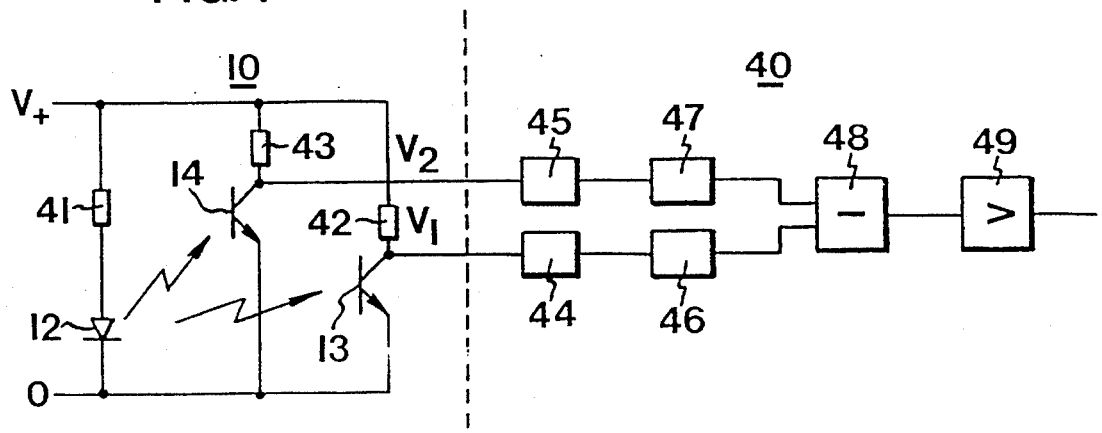

SMOKE AND VAPOR DETECTOR FOR MICROWAVE OVEN

This is a continuation of application Ser. No. 08/053,055, filed Apr. 26, 1993, abandoned.

This invention relates to a detector for microwave ovens. The detector is adapted to detect the presence of particles, such as smoke and water vapour, in the chamber of a microwave oven during a heating procedure.

When heated in a microwave oven, food normally gives off water vapour in a given phase of the heating procedure when the water in the food evaporates. The emission of vapour then indicates how the heating proceeds. It is known to provide a humidity sensor measuring the humidity of the chamber air, and to use the output signal from the humidity sensor for automatic control of the procedure. If heating takes place at too high a power level, edge scorching may occur in some cases, which can result in the emission of smoke. When the cooking time and the power level have been clearly misset, the food may catch fire or get charred, resulting in heavy smoke emission.

The object of this invention is to provide a detector which is of simple design and primarily is adapted to detect smoke emission in the oven chamber, thereby to prevent accidents as well as damage to the food. The detector should also be adapted for detecting water vapour, e.g. for automatic control of the procedure.

According to the invention, this object is achieved by a detector which is characterised by a transmitter designed to transmit electromagnetic radiation of optical nature and arranged in a compartment which is shielded from external radiation and which, during a heating procedure, is filled with air from the oven chamber; a first receiver arranged opposite to the transmitter and designed to receive direct radiation from the transmitter along a transmission path through the interior of the compartment; a second receiver shielded from direct radiation from the transmitter and designed to receive indirect or scattered radiation from the interior of the compartment, each receiver emitting an output signal that is a measure of the radiation received; and a signal-processing circuit which is connected to the receivers and in which the output signals therefrom are compared to indicate, upon a given change of the relative magnitude of the output signals, the presence in the chamber air of particles affecting the radiation transmission.

Suitably, the transmitter is an IR-light-emitting diode, and the receivers are phototransistors.

To effectively prevent external radiation from reaching the receivers, the transmitter and the receivers are conveniently arranged in a detector housing provided with an air inlet and an air outlet and having internally non-reflective walls, said housing being mounted in such a position outside the oven chamber that ventilation air from the chamber flows through the housing during a heating procedure.

When smoke or water vapour enters the detector housing, the direct radiation received by the first receiver is decreased, whereas the indirect or scattered radiation received by the second radiator is increased. In the case of smoke or vapour emission, the output signals from the two receivers thus change in opposite directions. To take advantage of this, the signal-processing circuit is preferably designed to generate a signal constituting the difference between a signal derived from the first receiver, and a signal derived from the second receiver, this difference signal being utilised as an alarm signal to indicate the emission of smoke or vapour. The use of a difference signal reduces the risk of a false alarm. While variations in the light intensity of the transmitter, as well as variations caused by coatings on the surfaces, affect the two receivers in the same direction and are suppressed by the subtraction, variations caused by smoke and vapour are reinforced.

Smoke and vapour emission during heating in a microwave oven is always a dynamic process, and the useful information resides in the signal change with time rather than in the absolute signal magnitude. In a preferred embodiment of the detector, the signal-processing circuit is therefore designed first to differentiate the output signals from the receivers, whereupon the difference signal, which is utilised as an alarm signal, is generated by subtraction of the differentiated signals.

In the foregoing, smoke and water vapour have been rated equal, since the detector essentially responds in the same way to both, namely by decreasing the output signal from one receiver and increasing the output signal from the other receiver. In actual practice, however, there is a considerable difference between the signal variations caused by smoke emission and those caused by vapour emission, both as to magnitude and time characteristic. It is therefore possible to discriminate between smoke and water vapour by imposing different requirements on the magnitude and the time derivatives of the signal variations.

Generally, the signal variations caused by smoke emission are much larger than those caused by vapour emission. The detector may, however, be rendered more sensitive to water vapour by a simple modification residing in the provision of a transparent partition in the transmission path between the transmitter and the first receiver, the second receiver being situated on the same side of the partition as the transmitter, and the partition cooperating with means for keeping the partition at a lower temperature than the chamber air.

Embodiments of the invention will be described in more detail below with reference to the accompanying drawing, in which FIG. 1 is an end view illustrating the basic design of the detector unit in a detector according to the invention, FIG. 2 is a cross-section of a simple embodiment of the detector housing of the detector unit, the housing being made in one piece, FIG. 3 is a perspective view of an oven chamber with a detector unit according to the invention attached on the outside of the chamber to illustrate a suitable position for the detector, FIG. 4 shows, to the left, a circuit diagram for the components of the detector unit and, to the right, a block diagram for the signal-processing circuit connected to the detector unit, and FIG. 5 is an end view similar to that of FIG. 1 and showing a modification of the detector according to the invention.

The detector unit 10 shown in FIG. 1 comprises a detector housing 11, a transmitter 12 for transmitting optical radiation or light radiation, and two receivers 13, 14 for receiving the optical radiation. Suitably, the transmitter 12 is an IR-light-emitting diode, and the receivers 13, 14 are phototransistors. The receiver 13 is mounted opposite to the transmitter 12 in the housing and receives direct radiation therefrom along a straight transmission path through the interior of the housing. The receiver 14 receives indirect or scattered radiation from the interior of the housing. A screen 15, provided between the transmitter 12 and the receiver 14, serves to prevent direct radiation from the transmitter 12 from reaching the receiver 14. The housing has non-reflective inner walls and is so designed that light radiation from the surroundings cannot be reflected and reach the receivers. Further, the housing is so mounted that ventilation air from the chamber of a microwave oven passes through the detector housing during a heating procedure.

FIG. 2 illustrates a simple embodiment of the detector housing, which is made in one piece in the form a square block 21 formed with three bores 22, 23, 24. By a suitable relative positioning of the centres of the bores, a portion of material 25 having the same function as the screen 15 in FIG. 1 remains after the boring operation. The bores form open channels, in each of which are mounted a transmitter and a receiver, respectively.

The detector unit is conveniently mounted in the space between the oven chamber and the outer casing of the microwave oven. A suitable position is shown in FIG. 3, where the oven chamber is designated 30 and the exhaust holes for ventilation air from the chamber are designated 31. In FIG. 3, the detector unit is mounted directly on the outside of the chamber at the exhaust holes and may, in the embodiment of the detector housing shown in FIG. 2, be mounted with its channels arranged vertically. Also other positions are conceivable, depending on how the air flow is guided in the space between the oven chamber and the outer casing.

In FIG. 4, which shows a circuit diagram for the electric components of the detector unit 10 as well as a simple block diagram for the following signal-processing circuit 40, the light-emitting diode 12 and the phototransistors 13, 14 are each connected in series with a resistor 41, 42 and 43, respectively, between a positive supply voltage $V_+$ and an earth potential 0. The output signals from the detector are formed by the voltage $V_1$ at the junction between the phototransistor 13 and the series resistor 42, and by the voltage $V_2$ at the junction between the phototransistor 14 and the series resistor 43, these voltages being supplied to the signal-processing circuit 40 for evaluation.

The detector operates as follows. In the idle state, the light-emitting diode 12 shines directly on the phototransistor 13, while only scattered light shines on the phototransistor 14. When smoke or vapour passes through the detector housing, the light to the phototransistor 13 is decreased, and the output voltage therefrom increases. Simultaneously, the smoke or vapour scatters the light, so that some light falls upon the phototransistor 14 and the output voltage therefrom decreases.

In the signal-processing circuit 40, the signals $V_1$ and $V_2$ are first equalised by filtering in equalising filters 44, 45. These filters suppress all rapid changes and 'spikes' caused by temporary disturbances as well as rapid periodical variations in the signals $V_1$, $V_2$, e.g. caused by the rotation of a bottom plate in the oven chamber, should such a plate be used for field equalisation. Then, the signals are differentiated in differentiating circuits 46, 47. These circuits have such a time constant, in the order of magnitude of seconds, that a signal variation with time that arises upon smoke or vapour emission, is reinforced by the differentiation, which makes it possible to achieve a prompter detection of smoke or vapour emission. The differentiation obviates the impact of slow variations in the signals, e.g. caused by drifts in different parameters. Finally, the differentiated signals are subtracted from one another in a subtraction circuit 48, and the difference signal from this circuit is amplified in an amplifier 49. The output signal from the amplifier 49 can be used as an alarm signal or for switching off the oven.

FIG. 5 shows a modification of the detector unit in FIG. 1, rendering the detector especially suitable for detecting water vapour. Compared with FIG. 1, the modification resides in the provision of a transparent partition 16 in the detector housing. The partition extends across the interior of the housing 11 between the phototransistor 13, on one hand, and the light-emitting diode 12 and the phototransistor 14, on the other. In the embodiment of FIG. 5, the phototransistor 13 thus receives the light that is let through the partition 16, while the phototransistor 14, which is situtated on the same side of the partition 16 as the light-emitting diode, receives the light that is scattered or reflected by the partition. Provided that the partition is maintained at a lower temperature than the air from the oven chamber, water vapour will condense on the partition, thereby affecting the output signals from the two phototransistors. To keep the partition 16 at a lower temperature than the chamber air, the partition can be in heat-conductive communication with the surroundings or be provided with special cooling fins.

I claim:

1. A detector adapted to detect the presence of particles of smoke and water vapour, in the chamber of a microwave oven during a heating procedure, said detector comprising a transmitter designed to transmit electromagnetic radiation of an optical nature and arranged in a compartment which is shielded from external radiation and which, during a heating procedure, is filled with air from the oven chamber; first and second receivers in said compartment filled with said air from the oven chamber; said first receiver arranged opposite to the transmitter and designed to receive direct radiation from the transmitter along a transmission path through the interior of the compartment; said second receiver shielded from direct radiation from the transmitter and designed to receive indirect or scattered radiation from the interior of the compartment, each receiver emitting an output signal that is a measure of the radiation received, the output signal from said first receiver changing in opposite direction to the output signal from said second receiver; and a signal-processing circuit which is connected to the receivers and in which the output signals therefrom are compared to indicate, upon a given change of the relative magnitude of the output signals, the presence in the chamber air of particles affecting the radiation transmission.

2. A detector as set forth in claim 1, wherein the transmitter is an IR-light-emitting diode, and the receivers are phototransistors.

3. A detector as set forth in claim 2, wherein the transmitter and the receivers are disposed in a detector housing provided with an air inlet and an air outlet and having internally non-reflective walls, said housing being mounted in such a position outside the oven chamber that ventilation air from the chamber flows through the housing during a heating procedure.

4. A detector as set forth in claim 1, wherein the signal-processing circuit comprises means for generating a signal constituting the difference between a signal derived from the first receiver, and a signal derived from the second receiver, this difference signal being utilised for indicating the presence of particles in the chamber air.

5. A detector as set forth in claim 4, wherein the signal-processing circuit comprises means for differentiating the output signals from the receivers, said difference signal being generated by subtraction of the differentiated signals.

* * * * *